United States Patent
Okumura et al.

(10) Patent No.: US 7,203,270 B2
(45) Date of Patent: *Apr. 10, 2007

(54) X-RAY COMPUTED TOMOGRAPHIC APPARATUS

(75) Inventors: Miwa Okumura, Kuroiso (JP); Masahiro Kazama, Shioya-gun (JP); Naofumi Watanabe, Nasu-gun (JP); Hideaki Takanezawa, Nasu-gun (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/819,977

(22) Filed: Apr. 8, 2004

(65) Prior Publication Data

US 2004/0202277 A1    Oct. 14, 2004

(30) Foreign Application Priority Data

Apr. 9, 2003    (JP) ............................. 2003-104834

(51) Int. Cl.
*A61B 6/00*    (2006.01)

(52) U.S. Cl. .................. 378/16; 378/109; 378/110; 378/901

(58) Field of Classification Search ............... 378/16, 378/109–112, 4, 15, 19, 20, 91, 207, 901; 382/131
See application file for complete search history.

(56) References Cited

U.S. PATENT DOCUMENTS

| | | | | |
|---|---|---|---|---|
| 5,103,469 A | | 4/1992 | Tanaka | 378/16 |
| 5,625,662 A | * | 4/1997 | Toth et al. | 378/16 |
| 5,696,807 A | | 12/1997 | Hsieh | 378/109 |
| 6,775,352 B2 | * | 8/2004 | Toth et al. | 378/108 |
| 7,031,423 B2 | * | 4/2006 | Tsukagoshi | 378/4 |
| 2004/0086076 A1 | * | 5/2004 | Nagaoka et al. | 378/4 |

FOREIGN PATENT DOCUMENTS

| | | |
|---|---|---|
| JP | 1-293844 | 11/1989 |
| JP | 4-54942 | 2/1992 |
| JP | 9-313476 | 12/1997 |
| JP | 2003-33346 | 2/2003 |
| JP | 2003-265459 | 9/2003 |

* cited by examiner

*Primary Examiner*—Edward J. Glick
*Assistant Examiner*—Jurie Yun
(74) *Attorney, Agent, or Firm*—Oblon, Spivak, McClelland, Maier & Neustadt, P.C.

(57) ABSTRACT

An X-ray computed tomographic apparatus includes a gantry, a reconstructing portion, and a tube current value determining portion. The gantry acquires projection data of an arbitrary range in a body axial direction by continuously moving a tabletop on which a subject is laid down and by continuously rotating an X-ray tube about the subject. The reconstructing portion reconstructs image data from the acquired projection data according to reconstruction processing selected by an operator from plural types of reconstruction processing. The tube current value determining portion determines plural tube current values respectively corresponding to discrete, plural positions within the range, on the basis of the selected type of reconstruction processing and an image quality level specified or selected by the operator.

16 Claims, 15 Drawing Sheets

FIG. 4A

UNIT: cm

| SCANOGRAM FOV | WATER PHANTOM DIAMETER (DW) |
|---|---|
| S | 24 |
| L | 40 |
| LL | 50 |

FIG. 4B

UNIT: CT NUMBER · PIXEL

| SCANOGRAM FOV | SECTOR INTEGRATION VALUE (AW) FOR ONE LINE OF WATER PHANTOM | | | |
|---|---|---|---|---|
| | 80kV | 100kV | 120kV | 135kV |
| S | 50000 | 50000 | 50000 | 50000 |
| L | 70000 | 70000 | 70000 | 70000 |
| LL | 80000 | 80000 | 80000 | 80000 |

FIG. 9

| Patient Information | Gantry Information | |
|---|---|---|

| No. | Start | Start Position | End Position | Scan Mode | No. of Scans | kV | mA ▼ | Scan Speed | High Quality | Reconstruction Mode | FOV | Helical Pitch |
|---|---|---|---|---|---|---|---|---|---|---|---|---|
| 1 | r | -978.5 | -1086.5 | Helical | 10 | 120 | | Auto | | construction | 282.5 | 4.0 |
| | | | | | | | | Others | Low dose | | | |
| | | | | | | | | 50 | SD5.0 | | | |
| | | | | | | | | 100 | SD6.0 | | | |
| | | | | | | | | 150 | SD7.0 | | | |
| | | | | | | | | 200 | SD8.0 | | | |
| | | | | | | | | 250 | SD9.0 | | | |
| | | | | | | | | 300 | SD10.0 | | | |
| | | | | | | | | 350 | | | | |

Main · Reconstruction Conditions · Window Conditions

[Copy] [Delete] [Back to Previous] [Confirm]

FIG. 12

| No. | Start | Start Position | End Position | Scan Mode | No. of Scans | kV | mA ▼ | Scan Speed | Reconstruction | FOV | Helical Pitch |
|---|---|---|---|---|---|---|---|---|---|---|---|
| 1 | r | -978.5 | -1086.5 | Helical | 10 | 120 | | Auto | High Quality construction | 282.5 | 4.0 |
| | | | | | | | | Others | Low dose | | |
| | | | | | | | | 50 | SD5.0 | | |
| | | | | | | | | 100 | SD6.0 | | |
| | | | | | | | | 150 | SD7.0 | | |
| | | | | | | | | 200 | SD8.0 | | |
| | | | | | | | | 250 | SD9.0 | | |
| | | | | | | | | 300 | SD10.0 | | |
| | | | | | | | | 350 | | | |

Patient Information

Gantry Information

Main | Reconstruction Conditions | Window Conditions

Copy | Delete | Back to Previous | Confirm

FIG. 13

X-RAY COMPUTED TOMOGRAPHIC APPARATUS

CROSS-REFERENCE TO RELATED APPLICATIONS

This application is based upon and claims the benefit of priority from prior Japanese Patent Application No. 2003-104834, filed Apr. 9, 2003, the entire contents of which are incorporated herein by reference.

BACKGROUND OF THE INVENTION

1. Field of the Invention

The present invention relates to an X-ray computed tomographic apparatus.

2. Description of the Related Art

As has been known, an X-ray computed tomographic apparatus is an apparatus that computes a spatial distribution of CT numbers on the basis of a quantity of X-rays absorbed in a subject's body. A CT number is defined as an X-ray absorption coefficient of tissues, such as organs, indicating a relative value (CT number) with respect to an X-ray absorption coefficient of water as the reference substance.

A reconstructed image contains image noises. A degree of image noises is typically given as a standard deviation of CT numbers within an image of a homogeneous phantom. In order to make a diagnosis by observing a reconstructed image, it is necessary to determine, for example, whether a small shadow on the image is a noise or a tumor. To this end, consideration must be given to an image SD (Standard Deviation) of the image being observed.

The image SD has strong tendency to depend on a transmission dose of X-rays, which is chiefly determined by a relation between a tube current and the subject.

The actual relation between the tube current and the image SD, however, is not a simple one-to-one correspondence, and varies with the body constitution of the subject and many other factors. It is therefore difficult to infer an image SD exactly, and hence to correct the tube current value adequately in response to the image SD. Also, in the case of helical scan, the tissue structure and the body thickness of the subject vary from region to region, and so does a transmission dose, which causes the image SD to vary with the reconstruction positions. This makes it difficult to read the image diagnostically or improves the image SD more than necessary for a diagnosis to be made.

BRIEF SUMMARY OF THE INVENTION

An object of the present invention is therefore to assist the setting of an optimal tube current value.

According to an aspect of the present invention, there is provided an X-ray computed tomographic apparatus including a gantry, a reconstructing portion, and a tube current value determining portion. The gantry acquires projection data of an arbitrary range in a body axial direction by continuously moving a tabletop on which a subject is laid down and by continuously rotating an X-ray tube about the subject. The reconstructing portion reconstructs image data from the acquired projection data according to reconstruction processing selected by an operator from plural types of reconstruction processing. The tube current value determining portion determines plural tube current values respectively corresponding to discrete, plural positions within the range, on the basis of the selected type of reconstruction processing and an image quality level specified or selected by the operator.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4A and FIG. 4B are views showing examples of constants used in S1 of FIG. 3;

FIG. 9 is a view showing the state where the item, "SD5.0", of FIG. 7 is selected;

FIG. 12 is a view showing the state where the item, "SD7.0", of FIG. 11 is re-selected;

FIG. 13 is a view showing a mA-to-position profile and a sample image displayed in pop-up windows in response to the click on the item, "SD7.0", of FIG. 12;

DETAILED DESCRIPTION OF THE INVENTION

One embodiment of an X-ray computed tomographic apparatus according to the invention will now be described with reference to the accompanying drawings. The X-ray computed tomographic apparatus includes various types, such as a rotate/rotate type in which a unit comprising the X-ray tube and the X-ray detector rotates about the subject, and a stationary/rotate type in which a number of detection elements are aligned in a ring-shaped array and the X-ray tube alone rotates about the subject, and the invention is applicable to any type. Herein, the currently most popular rotate/rotate type will be described. Also, in order to reconstruct tomographic data for one slice, it is necessary to obtain projection data of about 360° for a full circle of the subject, and projection data of 180° plus a view angle is needed even in the half scan method. The invention is applicable to either reconstruction method. Herein, the former method will be described by way of example. Also, popular mechanisms to convert incident X-rays to charges are: an indirect conversion scheme, by which X-rays are converted first into light by a fluorescent material, such as a scintillator, and the light is then converted to charges by a photoelectric converting element, such as a photodiode; and a direct conversion scheme, by which generation of electron-hole pairs in the semiconductor by X-rays and their movement to the electrodes, that is, the photoelectric phenomenon, are exploited. The X-ray detection elements adopting either scheme can be used, and herein, those adopting the former indirect conversion scheme will be described. In addition, a so-called multi-tube type X-ray computed tomographic apparatus, in which plural pairs of an X-ray tube and an X-ray detector are mounted to a rotational frame, has become commercially available recently, and the peripheral techniques are also under development. The invention is applicable to either a conventional single-tube type X-ray computed tomographic apparatus or a multi-tube type X-ray computed tomographic apparatus. Herein, a single-tube type X-ray computed tomographic apparatus will be described.

Figure 1:
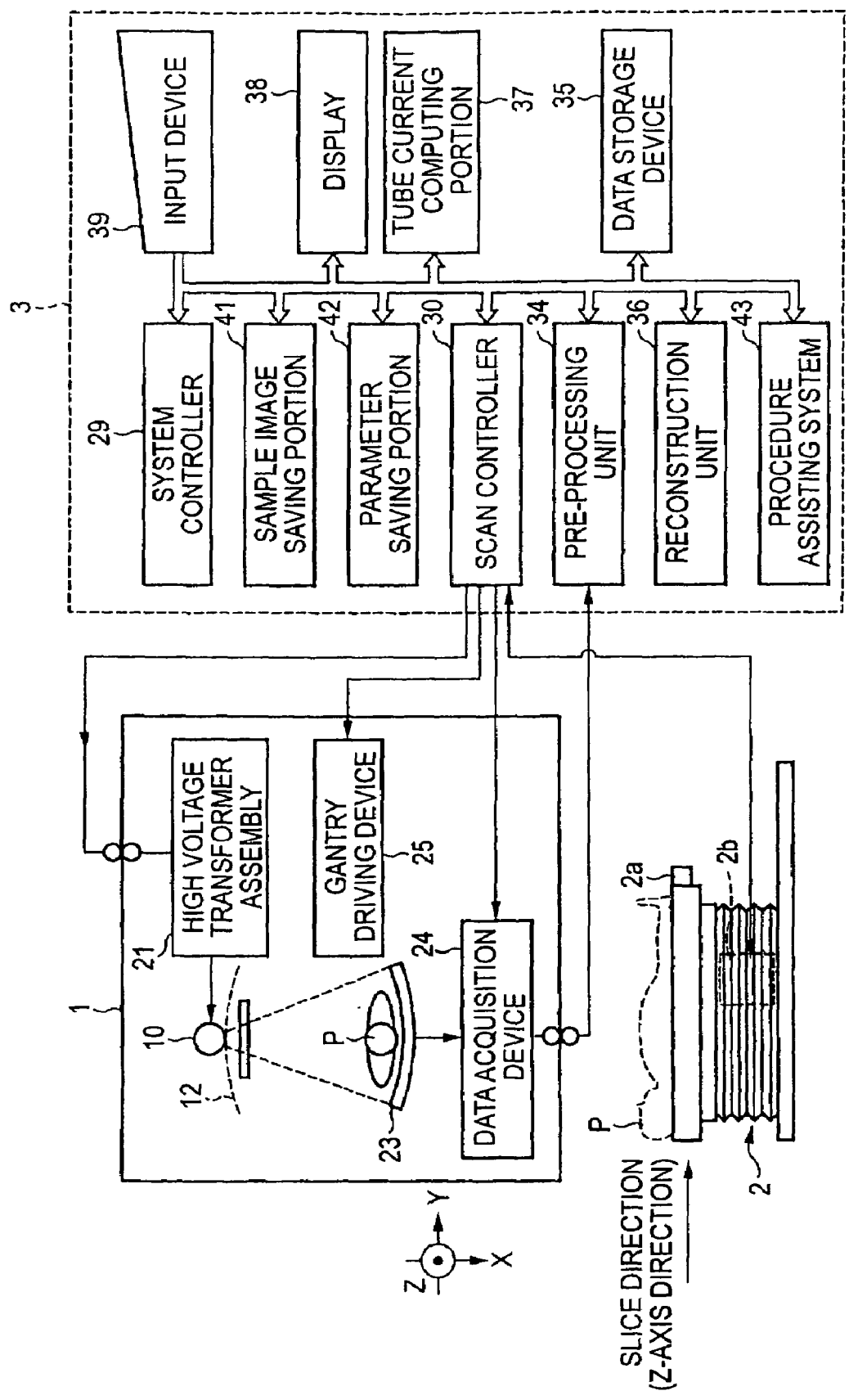
FIG. 1 is a view showing the configuration of an X-ray computed tomographic apparatus according to one embodiment of the invention.

FIG. 1 shows the configuration of the X-ray computed tomographic apparatus according to this embodiment. The X-ray computed tomographic apparatus includes a gantry 1 configured to acquire projection data related to the subject. The gantry 1 includes an X-ray tube 10 and an X-ray detector 23. Both the X-ray tube 10 and the X-ray detector 23 are mounted to a ring-shaped rotational frame 12, which is driven to rotate about the Z-axis by a gantry driving device 25. The rotational frame 12 is provided with an aperture at the center thereof, and the subject P laid on a tabletop 2a of a diagnostic table 2 is inserted into the aperture. A slit 22 used to vary the irradiation width of X-rays according to the slice thickness is placed between the X-ray tube 10 and the aperture. The diagnostic table 2 is provided with a tabletop driving portion 2b that moves the tabletop 2a in the major axis direction (parallel to the axis of rotation). The tabletop driving portion 2b includes a tabletop position detecting portion, such as a rotary encoder, to detect the position of the tabletop 2a.

A tube voltage from a high voltage transformer assembly 21 is applied between the cathode and the anode of the X-ray tube 10, while a filament current from the high voltage transformer assembly 21 is supplied to the filament of the X-ray tube 10. X-rays are generated by the application of the tube voltage and the supply of the filament current.

The X-ray detector 23 is a detector of either a single slice type or a multi-slice type. In the case of a single slice type, the X-ray detector 23 includes an array of elements in which more than one, for example, 916 X-ray detection elements each having, for example, a 0.5 mm×0.5 mm tetragonal light-reception surface, are aligned in a row along the channel direction. In the case of a multi-slice type, the X-ray detector 23 includes arrays of elements provided, for example, in 40 rows in parallel with each other along the slice direction.

A data acquisition device 24, generally referred to as a DAS (data acquisition system), converts a signal in each channel outputted from the detector 23 to a voltage signal, amplifies the voltage signal, and converts the amplified voltage signal to a digital signal. Data (raw data) thus obtained is fed to a computer unit 3 installed at the outside of the gantry. A pre-processing unit 34 of the computer unit 3 performs compensation processing, such as sensitivity compensation, on the raw data outputted from the data acquisition device 24, and outputs projection data. The projection data is then sent to and stored in a data storage device 35 of the computer system 3.

The computer system 3 comprises a system controller 29, an input device 39 provided with a keyboard, a mouse, etc., a display 38, a scan controller 30, a reconstruction unit 36, a procedure assisting system 43, a sample image saving portion 42, a tube current computing portion 37, and a parameter saving portion 42, in addition to the pre-processing unit 34 and the data storage device 35. The reconstruction unit 36 is pre-installed with reconstruction methods of several types, and reconstructs image data by the reconstruction method selected by the operator. The reconstruction methods of several types include, for example, the fan-beam reconstruction method (also referred to as the fan-beam convolution back projection method); and as a reconstruction method in a case where projection rays cross with the reconstruction plane diagonally, the Feldkamp method, known as an approximate image reconstruction method, by which convolution is performed by deeming the beam as a fan projection beam and the back projection is performed along the rays at the time of scans on the assumption that the cone angle is small, and the cone-beam reconstruction method, known as a method capable of suppressing cone-angle induced errors compared with the Feldkamp method, by which projection data is compensated for in response to the angle of rays with respect to the reconstruction plane.

Figure 2:
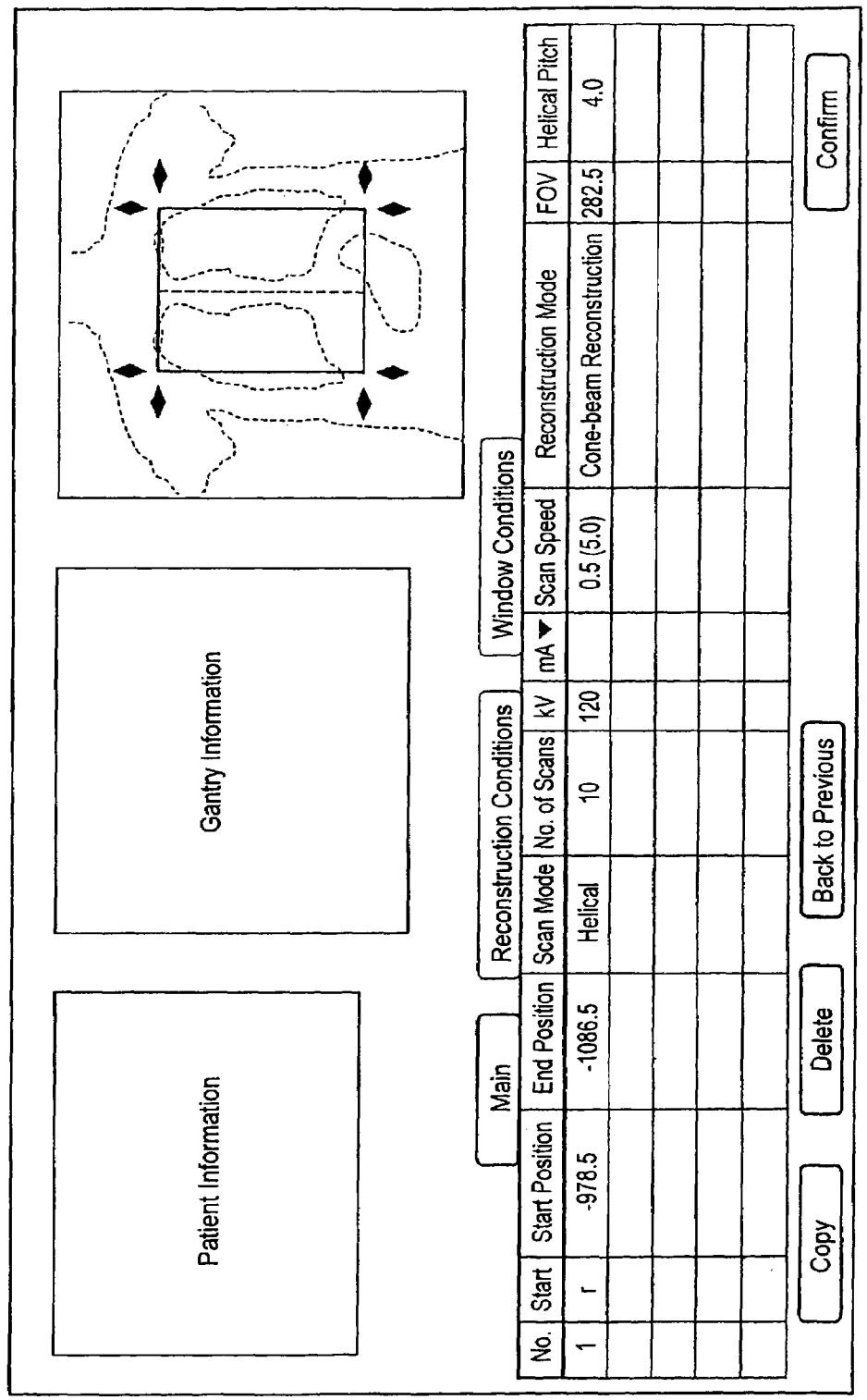
FIG. 2 is a view showing an example of a scan procedure screen constructed by a procedure assisting system of FIG. 1.

The procedure assisting system 42 is furnished with functions necessary to guide the operator interactively when he determines the scan procedure. For example, the procedure assisting system 42 constructs and displays a screen requesting the operator to input information as to the patient information, the purpose of examination, the region to be examined, etc. When the operator inputs the necessary information on the screen, the procedure assisting system 42 prepares a proposed scan procedure that best suit the information, and constructs and displays a screen requesting the operator to select or amend the proposed scan procedure. FIG. 2 shows an example of the scan procedure screen. On the scan procedure screen are displayed the patient information, gantry information, and a scanogram at the upper portion, and the details of the scan conditions at the lower portion. The scan conditions include plural items, such as the start position and the end position of helical scan associated with the frame line on the scanogram, the scan mode, the number of scans, the tube voltage (kV), the tube current (mA), the scan speed indicating the time needed for the X-ray tube 10 to rotate once (time in parentheses indicates the imaging time), the reconstruction mode, the field of view (FOV), and the helical pitch indicating a distance the tabletop moves at the scan speed.

Figure 6:
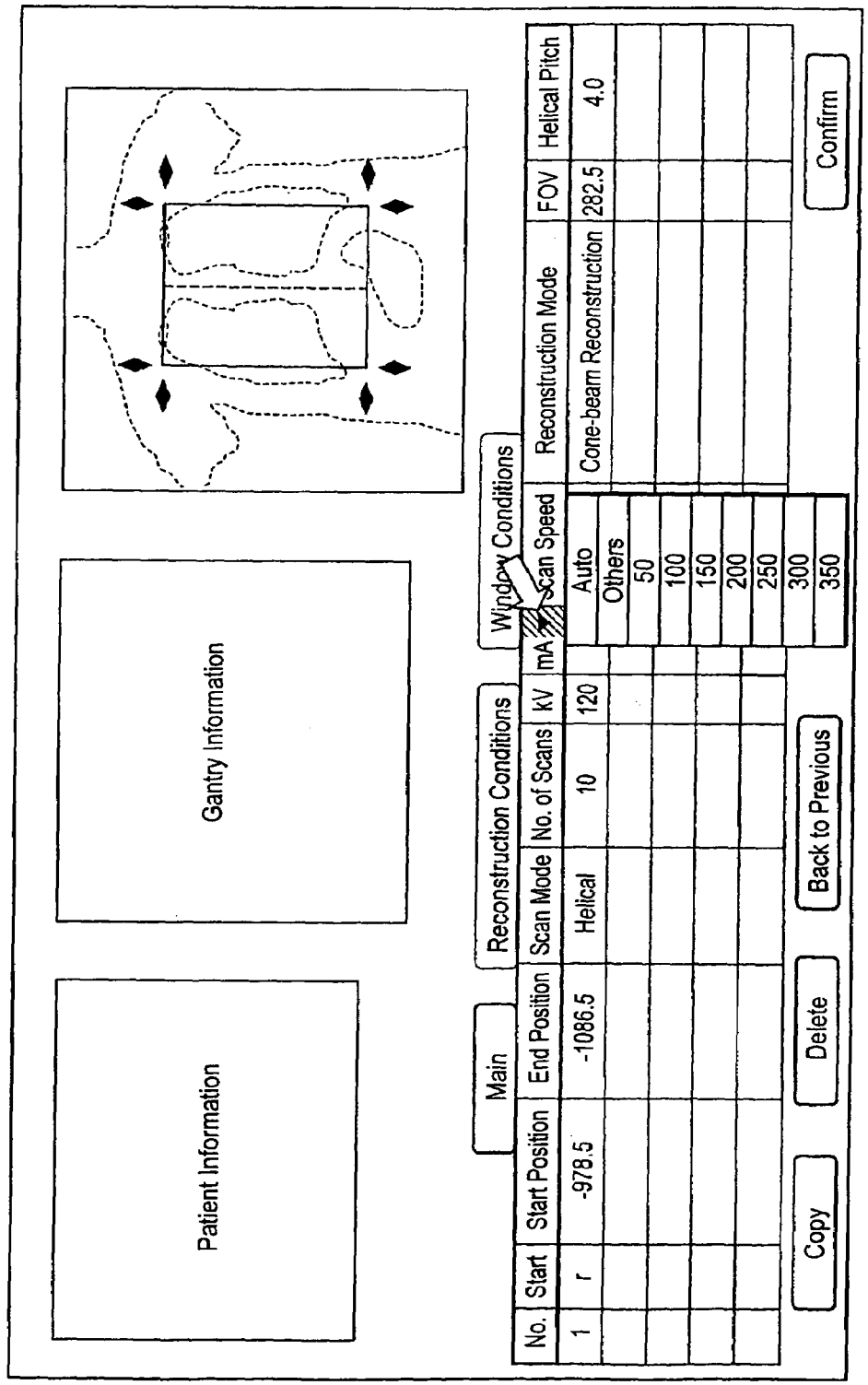
FIG. 6 is a view showing a pull-down menu in response to the click on the item, "mA", on the scan procedure screen of FIG. 2.
Figure 7:
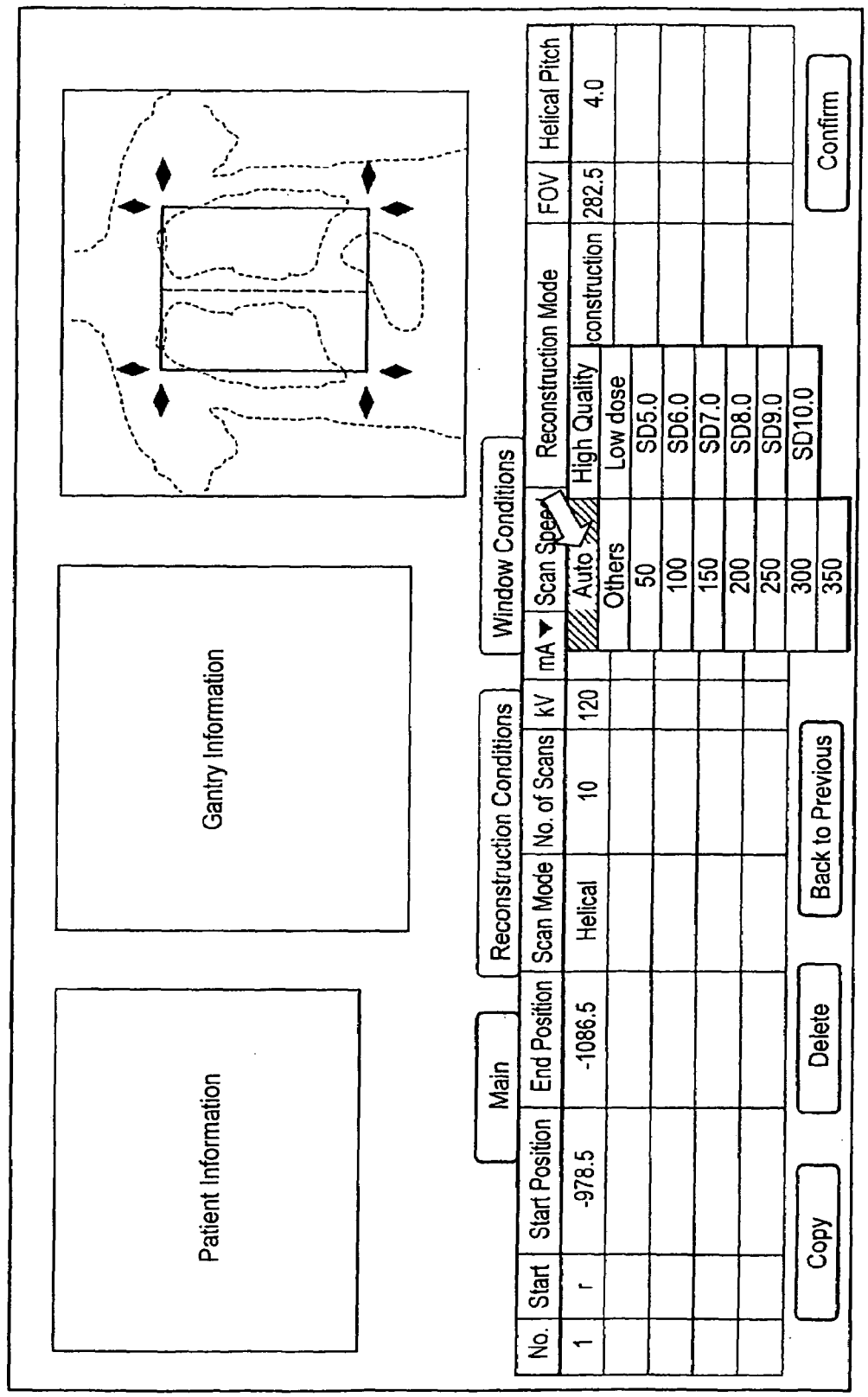
FIG. 7 is a view showing a pull-down menu in response to the click on the item, "Auto", of FIG. 6.

For the item of the tube current (mA), a pull-down menu is prepared together with a box into which the operator directly inputs a numerical value as the tube current value (see FIG. 6 and FIG. 7). Options prepared in the pull-down menu include plural tube current values as well as the automatic setting, "Auto". The automatic setting of the tube current value referred to herein is defined as the function to enable the system to automatically set a tube current value needed to achieve an image SD specified by the operator as an image SD used as the index of the image quality.

The sample image saving portion 42 saves data of plural sample images respectively corresponding to plural image SD's. The sample image is typically a tomographic image of a human body or a body-mimic phantom. When the operator selects a desired image SD, a sample image corresponding to the selected image SD is displayed.

The tube current computing portion 37 computes a tube current value needed to achieve the image SD selected by the operator. In practice, the tube current computing portion 37 is a ROM, and upon input of the necessary parameters, it computes and outputs a tube current value corresponding to the inputted parameters. The tube current value Ib is computed in accordance with the following equation:

$$Ib=(SDa^2/SDinput^2) \times (mAs/t) \times PkV \times Psl \times PHP \times PFW \times PFC \times Pmode \times \exp(-\mu(DPa-DPb))$$

where SDa is an image SD of an image of a water phantom having a water equivalent thickness DPa used as the reference, taken and reconstructed with the use of the reference tube current, the reference tube voltage, the reference imaging slice thickness, the reference image slice thickness, and the reference reconstruction function, SDinput is a desired image SD the operator wishes to obtain as the final image, mAs is a time-integrated tube current (sec) used as the reference, t is a scan speed (sec), PkV is a coefficient corresponding to a tube voltage, Psl is a coefficient corresponding to an imaging slice thickness, PHP is a coefficient corresponding to the helical pitch, PFW is a coefficient corresponding to a ratio of an image slice thickness with respect to an imaging slice thickness, PFC is a coefficient corresponding to a reconstruction function, Pmode is a coefficient corresponding to a normal mode or a low dose mode as to X-ray exposure, $\mu$ is an X-ray absorption coefficient of water, DPa is a water equivalent thickness (mm) used as the reference, and DPb is a water equivalent thickness (mm) equivalent to the subject's body thickness.

For the computation of the tube current value Ib, of all the foregoing parameters, SDa, mAs, DPa, and $\mu$ are given in advance as specified values. SDinput is inputted by the operator. Because t and PkV are set in the scan procedure, the tube current computing portion 37 inputs the set t and PkV from the procedure assisting system 43. Psl, PHP, PFC, and Pmode are respectively determined according to the imaging slice thickness, the helical pitch, the reconstruction function, and the exposure mode set in the scan procedure. Psl, PHP, PFC, and Pmode are determined in advance according to the imaging slice thickness, the helical pitch, the reconstruction function, and the exposure mode, respectively, and saved in the parameter saving portion 42. The tube current computing portion 37 inputs the set imaging slice thickness, helical pitch, reconstruction function, and exposure mode from the procedure assisting system 43, and thereby receives the corresponding coefficients Psl, PHP, PFC, and Pmode from parameter saving portion 42. Also, PFW is determined according to the imaging slice thickness and the image slice thickness set in the scan procedure. PFW is determined in advance according to various combinations of the imaging slice thickness and the image slice thickness, and saved in the parameter saving portion 42. The tube current computing portion 37 inputs the imaging slice thickness and the image slice thickness from the procedure assisting system 43, and thereby receives the corresponding coefficient PFW from the parameter saving portion 42.

In particular, of all the foregoing parameters, the imaging slice thickness coefficient Psl, the helical pitch coefficient PHP, and the coefficient PFW corresponding to the ratio of the image slice thickness with respect to the imaging slice thickness are determined in advance for respective types of reconstruction method, such as the fan beam reconstruction method, the Feldkamp method, and cone-beam reconstruction method, and saved in the parameter saving portion 42. The tube current computing portion 37 thus inputs the set imaging slice thickness, helical pitch, reconstruction function, and exposure mode as well as the type of reconstruction method from the procedure assisting system 43, and thereby receives the coefficients Psl, PHP, PFC, and Pmode corresponding to their respective values and the type of reconstruction method from the parameter saving portion 42. It is thus possible to determine a tube current value that achieves the selected image SD with a high degree of accuracy, according to the selected type of reconstruction processing.

The water equivalent thickness DPb equivalent to the subject's body thickness is specified by the tube current computing portion 37 for each of plural tabletop positions corresponding to the reference rotational position (for example, the position at 0°) of the X-ray tube 10 repeated during the helical scan, with the use of scanogram data. A method of finding the water equivalent thickness DPb will be described below.

Circular cylindrical water phantoms of several types having different diameters as set forth in FIG. 4A are prepared. For example, a water phantom S having a diameter DW of 24 cm, a water phantom L having a diameter DW of 40 cm, and a water phantom LL having a diameter DW of 50 cm are prepared. These water phantoms S, L, and LL are placed in the field of view in such a manner that the central axis of each circular cylinder agrees with the central axis of rotation of the X-ray tube 10, and a scanogram at the reference rotational position (for example, the position at 0°) is taken for each phantom. An integration value SW of pixel values of plural pixels within a rectangular region (m×n pixels) of a predetermined size in the vicinity of the center of the scanogram is found for each of the water phantoms S, L, and LL. Herein, m is a predetermined number of pixels in the channel direction that cover a phantom image except for the mask portions at the both ends of the scanogram, and n is a predetermined number of pixels in the body axial direction (slice direction).

The integration value SW found for each of the water phantoms S, L, and LL is divided by n to compute an average integration value AW for one line (a line comprising m pixels in the channel direction×1 pixel in the body axial direction). The average integration value AW for one line is found for each of the water phantoms S, L, and LL. Further, AW's at various tube voltages are found in the same manner (see FIG. 4B). In practice, these AW's are found in advance and the data thereof is saved in the parameter saving portion 42.

Figure 5:
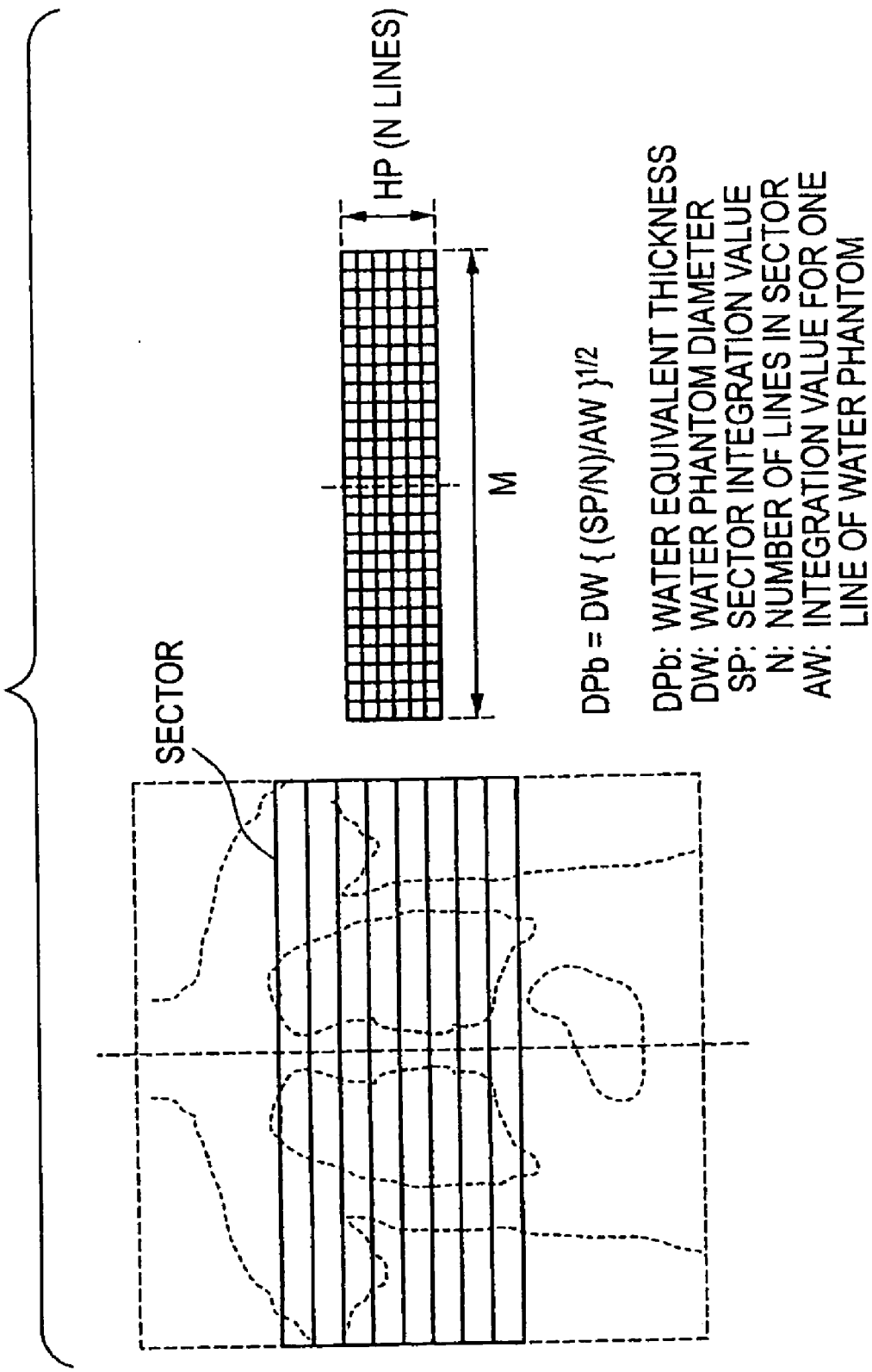
FIG. 5 is a supplemental view of a water equivalent thickness computing method in S1 of FIG. 3.

Subsequently, as is shown in FIG. 5, plural sectors are set in the scanogram obtained by imaging the subject to be examined at the reference rotational position (for example, the position at 0°). Each sector is of a size of M×N pixels. M is the number of pixels in a region of the scanogram except for the mask portions at the both ends, and is equal to m. N is determined according to the rotational cycle during the helical scan in the body axial direction, that is to say, it is set to the number of pixels corresponding to the helical pitch HP. The integration value SP of the pixel values in each sector is found.

The water equivalent thickness DPb of the subject is found in accordance with the following equation:

$$DPb=DW\times((SP/N)/AW)^{1/2}$$

where AW is the integration value and DW is the diameter of the water phantom S, L, or LL having the diameter in close proximity to the subject's body constitution, SP is the integration value in the sectors of the scanogram of the subject, and N is the number of pixels corresponding to the helical pitch HP. In other words, a ratio of the integration value AW of the water phantom for one line and the integration value SP/N of the subject is an area ratio, and in order to convert the area ratio to a diameter ratio, the square root is found, which is multiplied by the diameter DW of the water phantom used as the reference.

The water equivalent thickness DPb is computed at each of discrete, plural positions at intervals equal to the helical pitch in the body axial direction within the scan range in each sector, by performing the computation in the same manner for each sector. Then, plural tube current values Ib's respectively corresponding to discrete, plural positions in the body axial direction within the scan range according to the rotational cycle are computed, on the basis of the water equivalent thickness DPb's corresponding to these plural positions and other parameters. When the helical scan is performed, the scan controller 30 dynamically controls the tube current of the X-ray tube 10 according to the plural tube current values I's thus computed. It is thus possible to maintain the operator-specified image SD for an image SD in the body axial direction.

Figure 8:
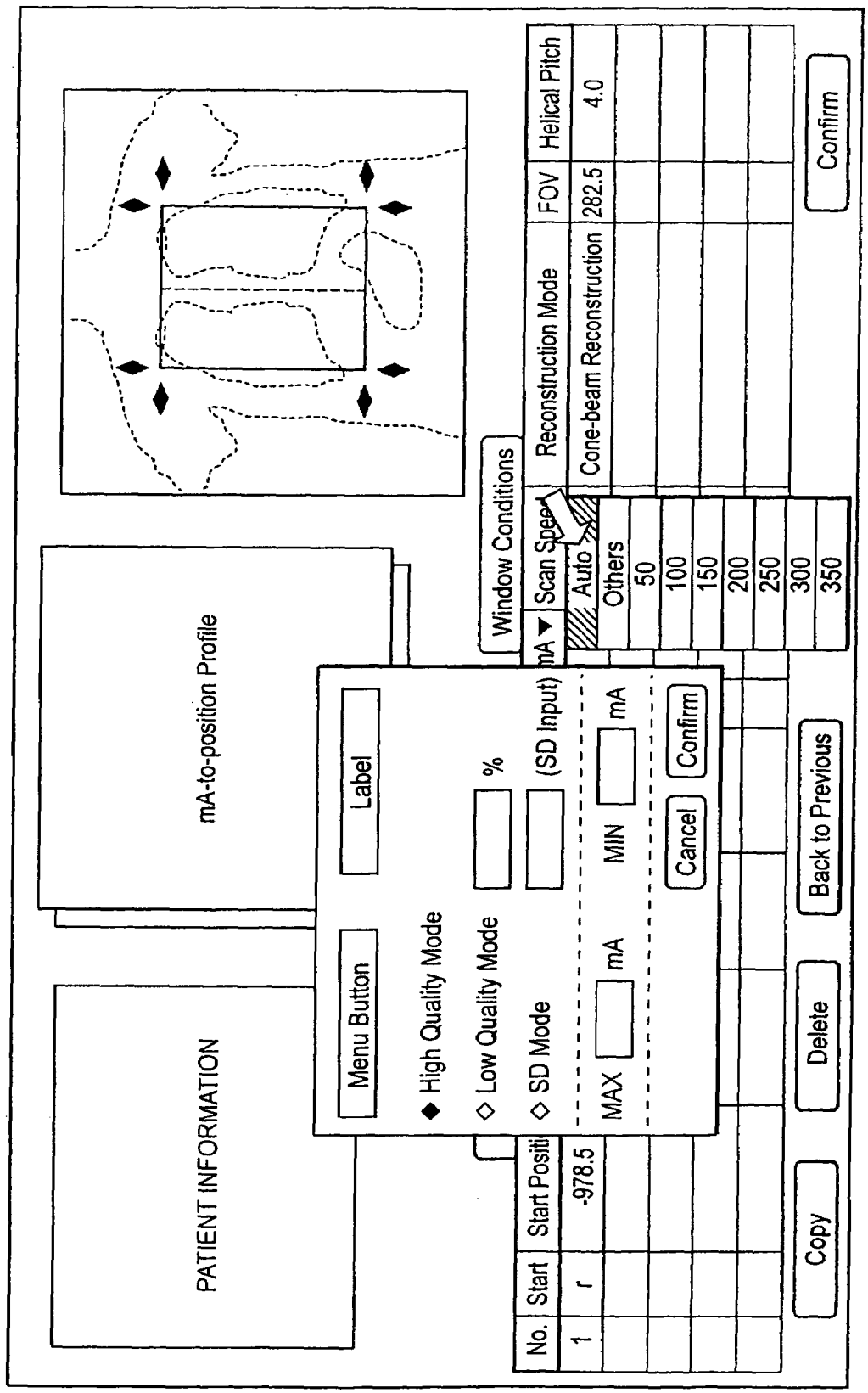
FIG. 8 is a view showing a pop-up menu in response to the click on the item, "Auto", of FIG. 6.

The setting procedure of the tube current in this embodiment will now be described. The scan procedure screen constructed by the procedure assisting system 43 as is shown in FIG. 2 is displayed on the display 38. As is shown in FIG. 6, when the operator clicks on the tube current (mA) item, the pull-down menu is displayed. The operator either selects a desired tube current value or clicks on "Auto" in the pull-down menu. "Auto" corresponds to an activation command for the function to automatically set the tube current value corresponding to the specified image SD. When "Auto" is clicked, a pull-down menu shown in FIG. 7 to select the image SD is displayed or a menu shown in FIG. 8 to select the image SD is displayed in a pop-up window. The pull-down menu shown in FIG. 7 includes "High Quality", "Low Dose", and plural options for the value of the image SD. The menu of FIG. 8 includes a box used to directly input a ratio of the X-ray dose in the low dose mode with respect to the X-ray dose in the high quality mode, a box used to directly input a value of the image SD, a box used to directly input the maximum value of the tube current, and a box used to directly input the minimum value of the tube current, in addition to the options including "High Quality Mode", "Low Dose Mode", and "SD mode". Herein, an explanation will be given on the assumption that the pull-down menu shown in FIG. 7 is used.

Figure 10:
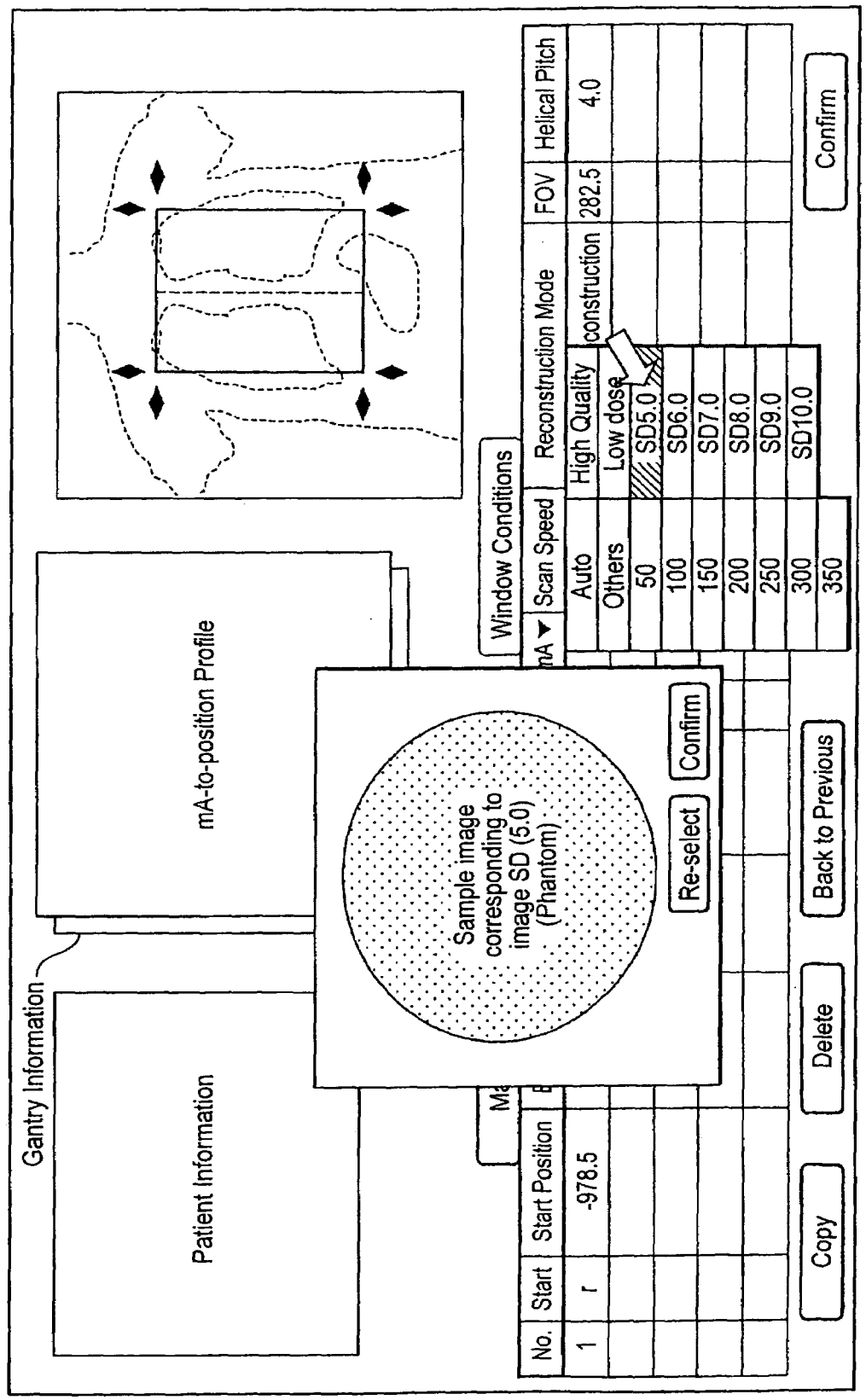
FIG. 10 is a view showing a mA-to-position profile and a sample image displayed in pop-up windows in response to the click (execution of the selection) on the item, "SD5.0", of FIG. 9.

As is shown in FIG. 9, when "SD5.0", corresponding to an action to automatically set the tube current value according to the image SD5.0, is selected and clicked, a mA-to-position profile (graph) indicating a spatial change of the tube current value by correlating the tube current value with the tabletop position and a sample image corresponding to the image SD5.0 selectively read out from the sample image saving portion 41 are displayed in the pop-up windows as is shown in FIG. 10.

Figure 3:
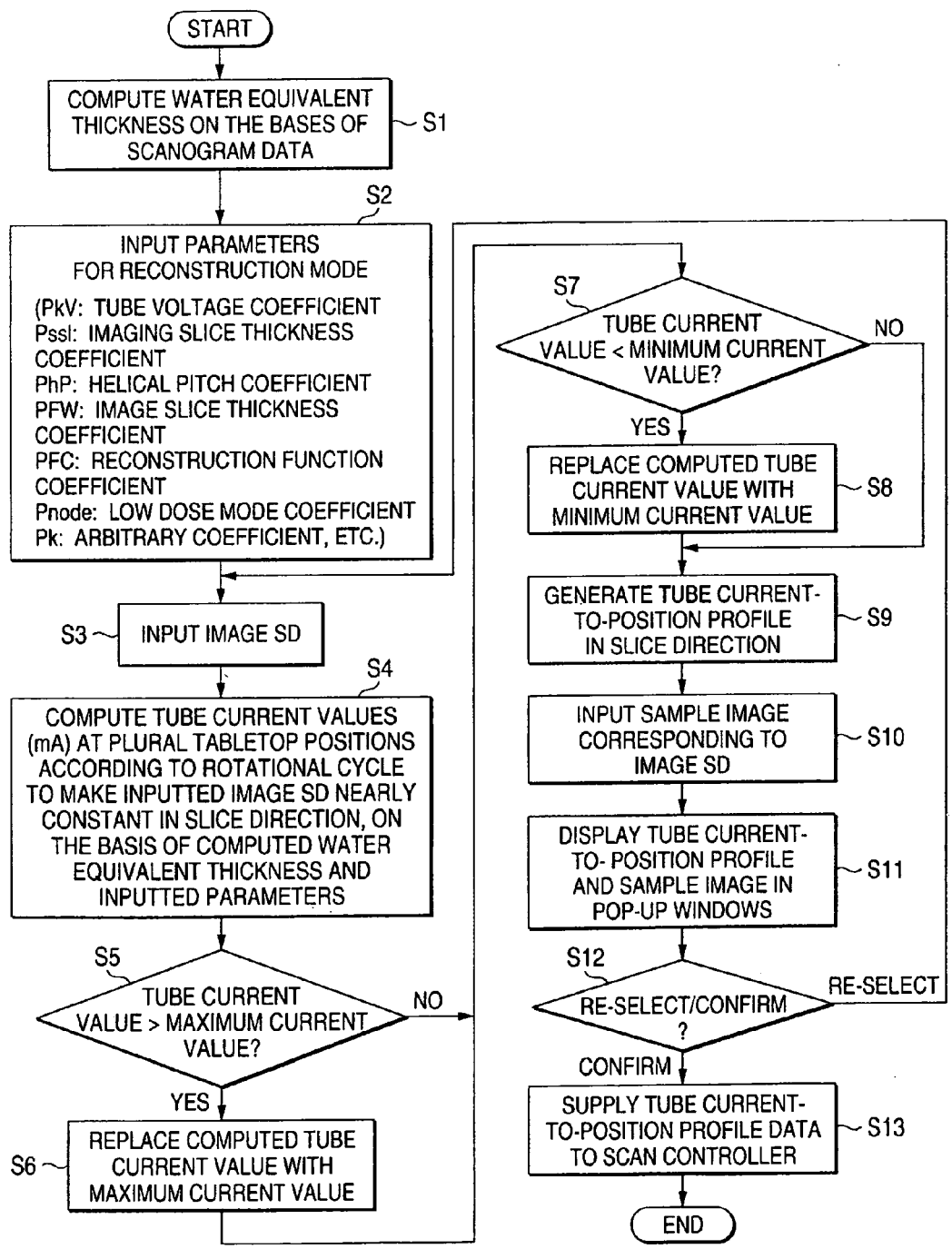
FIG. 3 is a flowchart detailing the tube current computation processing by a tube current computing portion of FIG. 1.

In order to prepare the mA-to-position profile, as is detailed in FIG. 3, the tube current computing portion 37 computes the water equivalent thickness DPb equivalent to the subject's body thickness for each of plural tabletop positions corresponding to the reference rotational position (for example, the position at 0°) of the X-ray tube 10 repeated during the helical scan with the use of the scanogram data, as has been described above (S1). Subsequently, parameters, such as the tube voltage coefficient PkV, corresponding to the reconstruction mode, such as the cone-beam reconstruction mode, and set on the scan procedure screen are read out from the parameter saving portion 42 to the tube current computing portion 37 (S2). The image SD is then inputted to the tube current computing portion 37, and the tube current value is computed on the basis of the parameters, such as the computed water equivalent thickness DPb and the inputted tube voltage coefficient PkV in such a manner that the image SD5.0 thus inputted is maintained at the respective tabletop positions (S4). Each of the tube current values thus computed is compared with the maximum current value specified to comply with the safety standard or the initially set maximum current value (S5). When the computed tube current value is larger than the maximum current value, the maximum current value is correlated with this tabletop position instead of the computed tube current value (S6). When the computed tube current value is equal to or smaller than the maximum current value, the computed tube current value is correlated with this tabletop position. Likewise, each of the computed tube current values is compared with the initially set minimum current value (S7). When the computed tube current value is smaller than the minimum current value, the minimum current value is correlated with this tabletop position instead of the computed tube current value (S8). When the computed tube current value is equal to or larger than the minimum current value, the computed tube current value is correlated with this tabletop position.

Figure 11:
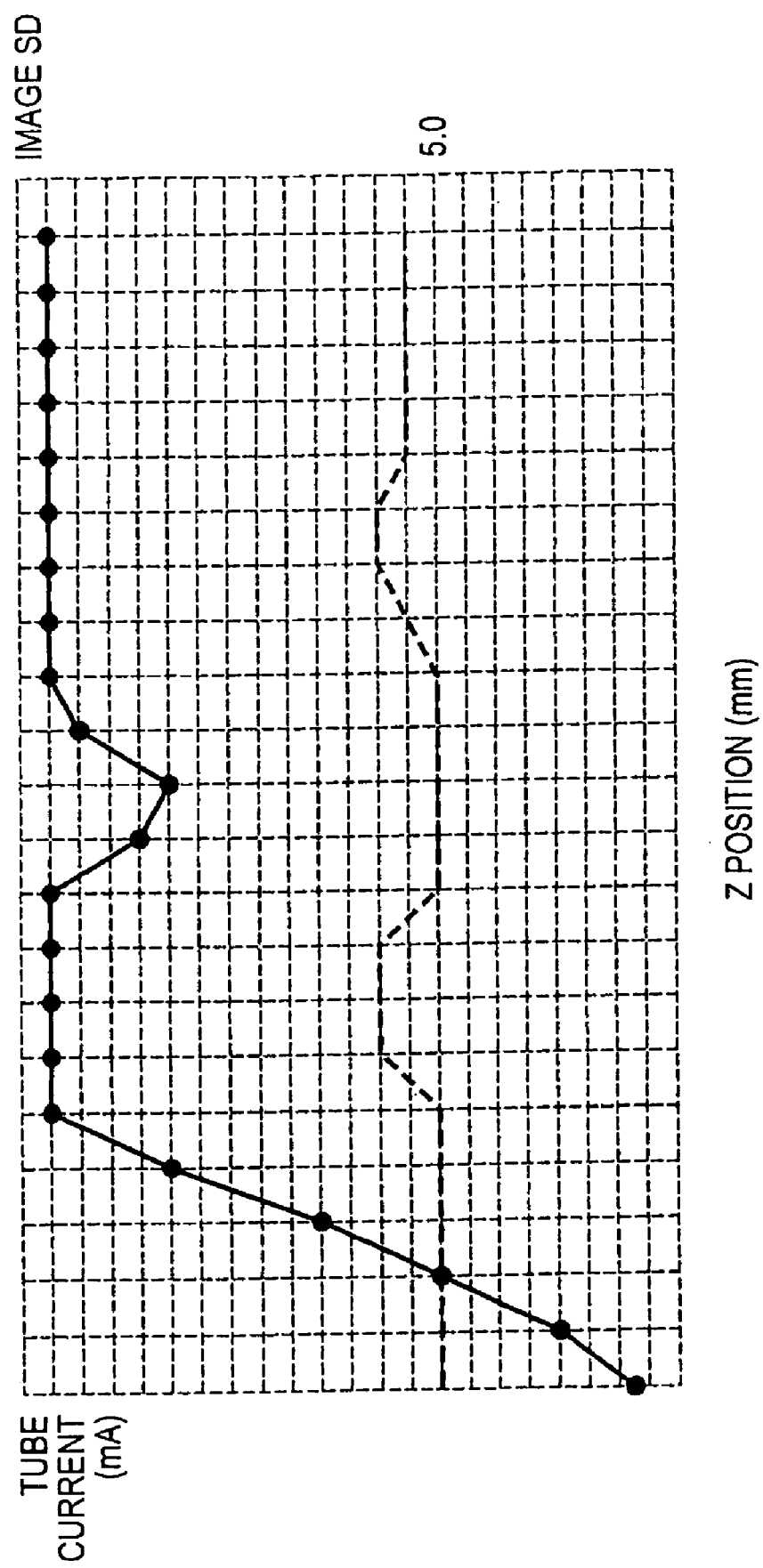
FIG. 11 is a view showing an example of a mA-to-position profile of FIG. 10.

The tube current computing portion 37 then prepares the mA-to-position profile that indicates the tube current value corresponding to the image SD5.0 in connection with the table position as is shown in FIG. 11 by way of example, on the basis of the correspondence of plural tube current values with the plural tabletop positions (S9). It should be noted that the mA-to-position profile includes the image SD profile indicating the image SD in connection with the tabletop position. At the tabletop position at which the computed tube current value is replaced with the maximum current value, the image SD is higher than 5.0. Also, at the tabletop position at which the computed tube current value is replaced with the minimum current value, the image SD is smaller than 5.0. The tube current computing portion 37 then computes the image SD at the tabletop position where the replacement took place, on the basis of the replaced maximum or minimum tube current value.

Figure 13:
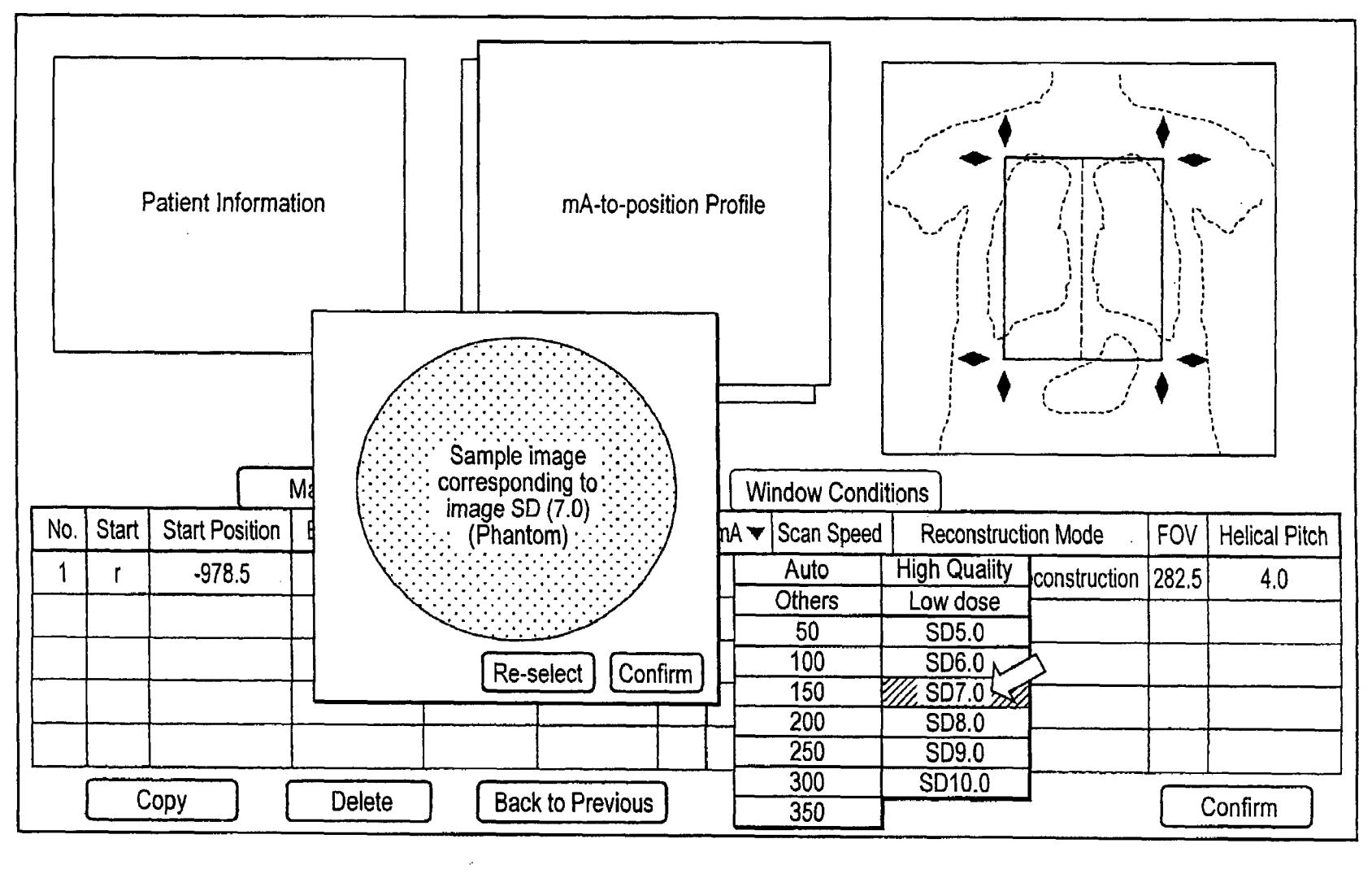
Figure 14:
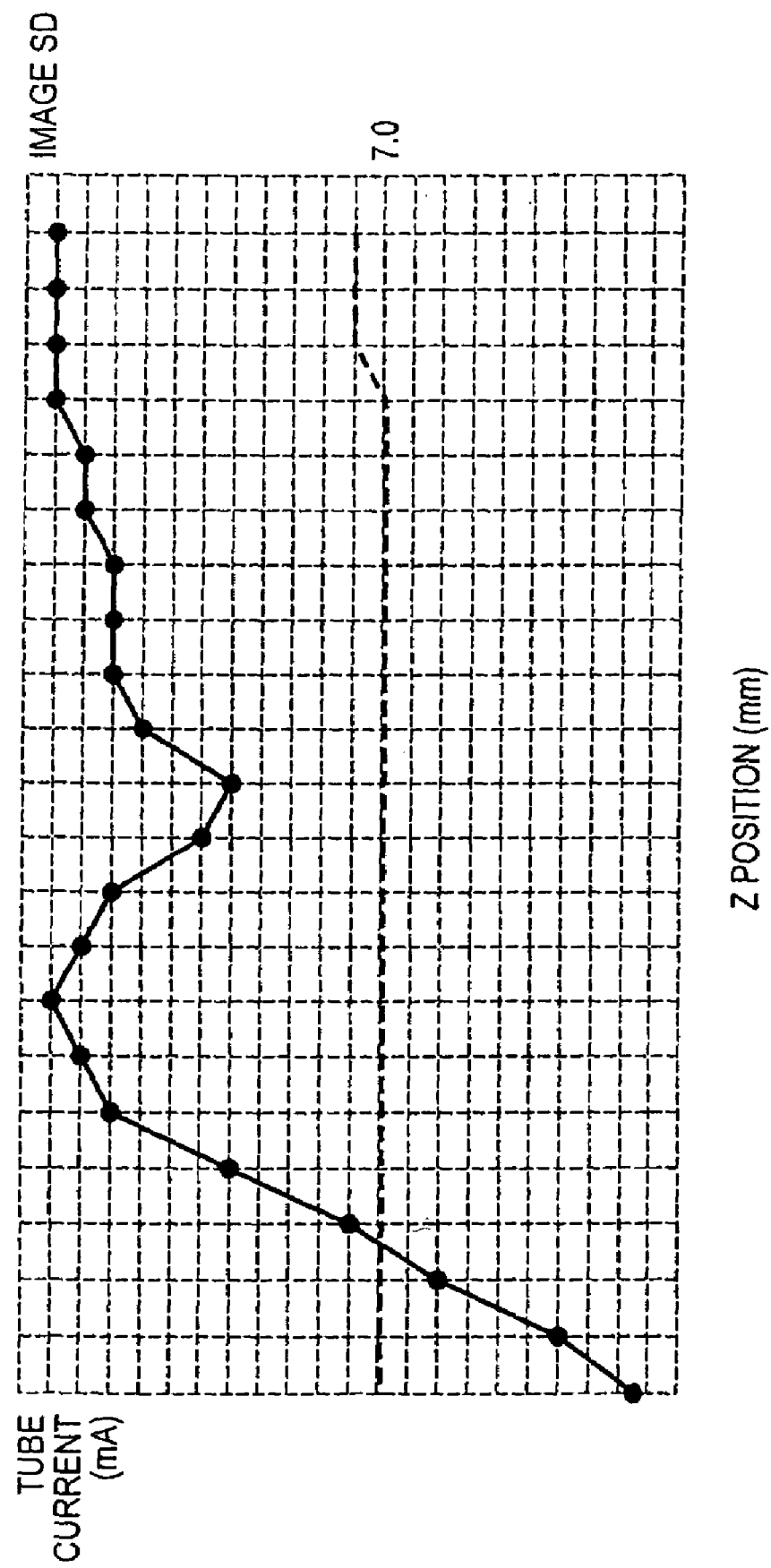
FIG. 14 is a view showing an example of a mA-to-position profile of FIG. 13.

The procedure assisting system 43 displays, in the pop-up windows on the display 38, a sample image of the water phantom corresponding to the image SD5.0 inputted from the sample image saving portion 41 (S10), and the mA-to-position profile prepared in the tube current computing portion 37 (S11). When the operator clicks on a "RE-SELECT" button (S12), the pull-down menu is displayed as is shown in FIG. 12. When "SD7.0", corresponding to an action to automatically set the tube current value according to the image SD7.0, is re-selected from the pull-down menu and clicked, the mA-to-position profile (see FIG. 14) corresponding to the image SD7.0 and a sample image of the water phantom corresponding to the image SD7.0 are displayed in the pop-up windows as is shown in FIG. 13 through the processing from S4 through S10.

When the operator confirms the mA-to-position profile and the sample image and clicks on a "CONFIRM" button (S12), data related to plural tabletop positions and the tube current values corresponding to the respective positions is supplied from the procedure assisting system 43 to the scan controller 30 (S13).

Figure 15:
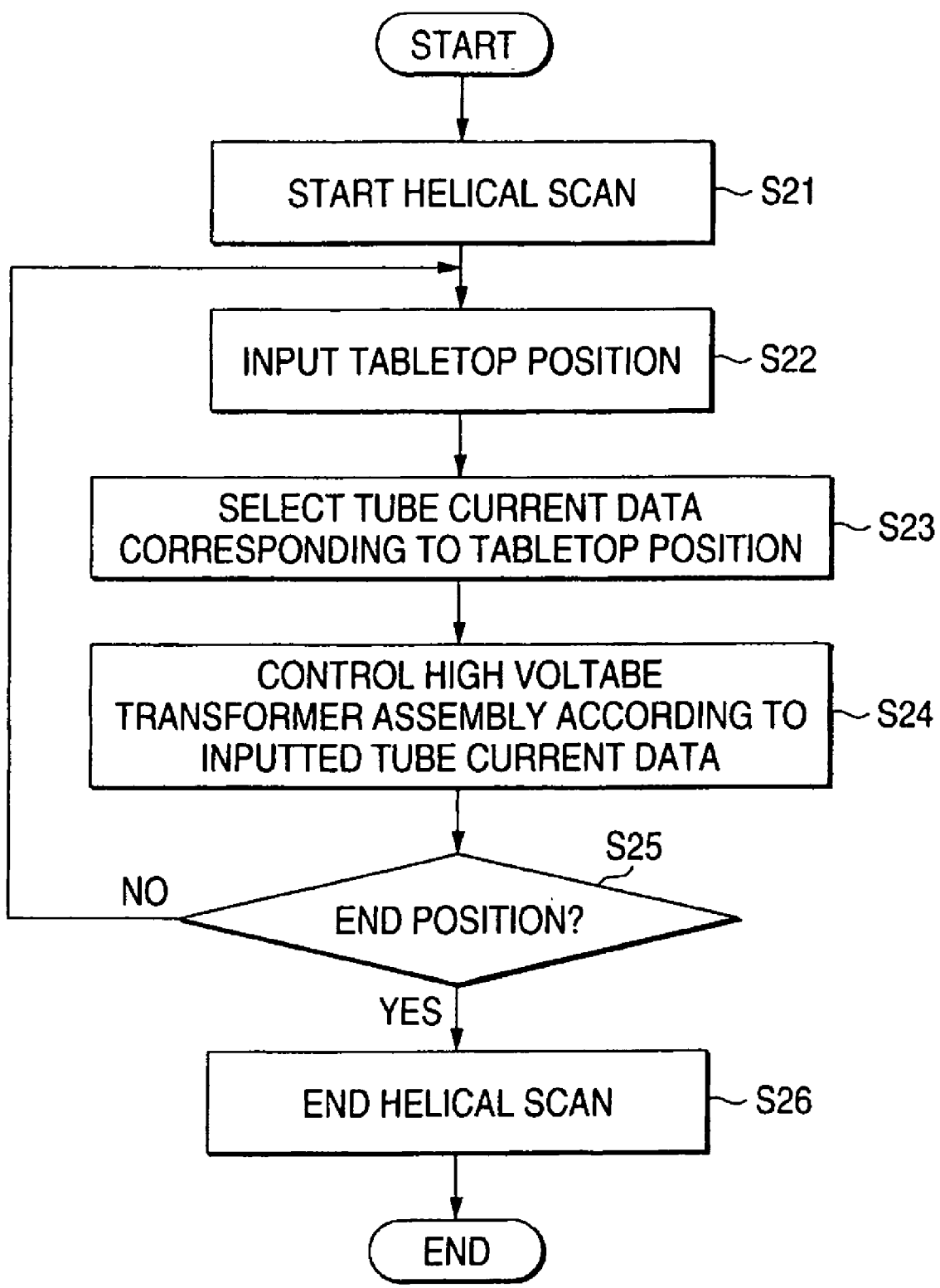
FIG. 15 is a flowchart detailing the processing procedure for image SD constant control by a scan controller of FIG. 1.

As is detailed in FIG. 15, when the helical scan is started (S21), a tabletop position signal is supplied from time to time from the tabletop position detecting portion in the tabletop driving portion 2b of the diagnostic table 2 to the scan controller 30 (S22). The scan controller 30 then selectively reads out the tube current value corresponding to the tabletop position (S23), and controls the high voltage transformer assembly 21 according to the tube current value thus read out. In practice, the scan controller 30 adjusts the filament current in the high voltage transformer assembly 21 in such a manner that the tube current of the X-ray tube 10 agrees with the selected tube current value. Because the tube current value is determined for each of discrete tabletop positions at intervals equal to the helical pitch, as described above, there may be a case that the tube current value corresponding to a given tabletop position is absent. In such a case, the tube current being present is maintained. The processing from S22 through S24 is continued until the tabletop position reaches the predetermined end position (S25). In this embodiment, because the tube current value is determined for each of discrete tabletop positions at intervals equal to the helical pitch, the tube current value is adjusted dynamically each time the X-ray tube 10 rotates once in sync with the rotational cycle during the helical scan. However, by determining the tube current value for each of discrete tabletop positions at intervals shorter than the helical pitch, it is possible to adjust the tube current more minutely at shorter intervals, such as 5° and 10°, during one rotation.

As has been described, according to this embodiment, because the tube current value is determined to achieve the operator-specified image quality (image SD), the operator is able to obtain an image at the intended image quality, which in turn reduces occasions for operations, such as performing the scans all over again. In addition, because the tube current value is determined by taking the water equivalent thickness, the type of reconstruction processing, and the helical pitch into account, the intended image quality can be achieved with enhanced accuracy. Moreover, when the operator sets the image quality, a profile indicating the tube current values in connection with plural positions, a profile indicating the image qualities in connection with plural positions, and the sample image are displayed. The operator is thus able to understand the image quality visually, which makes the image quality setting work easier. Further, by dynamically controlling the tube current of the X-ray tube 10 according to plural tube current values respectively corresponding to the determined plural tabletop positions, it is possible to maintain the image quality in the body axial direction at or nearly at a constant level.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomographic apparatus, comprising:
    an X-ray tube;
    a gantry configured to acquire projection data of an arbitrary range in a body axial direction of a subject by continuously moving a tabletop on which said subject is laid down and by continuously rotating said X-ray tube about said subject;
    a reconstructing portion configured to reconstruct image data from said acquired projection data according to reconstruction processing selected by an operator from plural types of reconstruction processing; and
    a tube current value determining portion configured to determine plural tube current values respectively corresponding to discrete, plural positions within said range, on the basis of said selected type of reconstruction processing and an image quality level specified or selected by said operator;
    wherein a particular tube current value, $I_b$, is determined on the basis of SD (SDinput), mAs, PkV, Psl, PFW, PFC, SDa, t, PHP, Pmode, $\mu$, DPa, and DPb,
    where SDa is an image SD of an image of a water phantom having a water equivalent thickness DPa used as the reference, taken and reconstructed with the use of a reference tube current, a reference tube voltage, a reference imaging slice thickness, and a reference image slice thickness, and a reference reconstruction function,
    SDinput is a desired image SD the operator wishes to obtain as the final image,
    mAs is a time-integrated tube current (sec) used as the reference,
    t is a scan speed (sec),
    PkV is a coefficient corresponding to a tube voltage,
    Psl is a coefficient corresponding to an imaging slice thickness,
    PHP is a coefficient corresponding to the helical pitch,
    PFW is a coefficient corresponding to a ratio of an image slice thickness with respect to an imaging slice thickness,
    PFC is a coefficient corresponding to a reconstruction function,
    Pmode is a coefficient corresponding to a normal mode or a low dose mode as to X-ray exposure,
    $\mu$ an X-ray absorption coefficient of water,
    DPa is a water equivalent thickness (mm) used as the reference, and
    DPb is a water equivalent thickness (mm) equivalent to the subject's body thickness.

2. The X-ray computed tomographic apparatus according to claim 1, wherein:
    said image quality level is one of a standard deviation of CT numbers and a low-contrast resolution related to an image of a homogeneous phantom.

3. The X-ray computed tomographic apparatus according to claim 1, further comprising: a control portion that dynamically controls a tube current of said X-ray tube in association with movement of said tabletop, according to said determined plural tube current values.

4. The X-ray computed tomographic apparatus according to claim 1, wherein:

said tube current values are determined in a range from a maximum tube current value to a minimum tube current value.

5. The X-ray computed tomographic apparatus according to claim 1, wherein:
intervals among said plural positions are set equal or nearly equal to a distance said tabletop moves while said X-ray tube rotates once.

6. The X-ray computed tomographic apparatus according to claim 1, wherein:
said tube current values are determined in such a manner that said image quality level specified or selected by said operator is maintained at the plural positions within said range.

7. The X-ray computed tomographic apparatus according to claim 1, wherein:
a water equivalent thickness estimated from data of a scanogram of said subject is used to determine said tube current values.

8. The X-ray computed tomographic apparatus according to claim 1, further comprising:
a sample image display portion configured to display a sample image corresponding to said image quality level specified or selected by said operator.

9. The X-ray computed tomographic apparatus according to claim 8, further comprising:
a sample image storage portion configured to store data of plural sample images corresponding to plural image quality levels.

10. The X-ray computed tomographic apparatus according to claim 1, wherein:
said tube current value determining portion determines said tube current values on the basis of a distance said tabletop moves while said X-ray tube rotates once or an index thereof as well as said type of reconstruction processing and said image quality level.

11. The X-ray computed tomographic apparatus according to claim 1, further comprising:
a display portion configured to display a graph showing a spatial change of tube current values corresponding to said plural tube current values together with a graph showing a spatial change of said image quality level.

12. An X-ray computed tomographic apparatus, comprising:
an X-ray tube;
a gantry configured to acquire projection data of an arbitrary range in a body axial direction of a subject by continuously moving a tabletop on which said subject is laid down and by continuously rotating said X-ray tube about said subject;
a reconstructing portion configured to reconstruct image data from said acquired projection data; and
a tube current value determining portion configured to determine plural tube current values respectively corresponding to plural positions within said range, on the basis of a distance, specified or selected by an operator, that said tabletop moves while said X-ray tube rotates once or an index thereof, and an image quality level specified or selected by said operator;
wherein a particular tube current value, $I_b$, is determined on the basis of SD (SDinput), mAs, PkV, Psl, PFW, PFC, SDa, t, PHP, Pmode, $\mu$, DPa, and DPb,
where SDa is an image SD of an image of a water phantom having a water equivalent thickness DPa used as the reference, taken and reconstructed with the use of a reference tube current, a reference tube voltage, a reference imaging slice thickness, and a reference image slice thickness, and a reference reconstruction function,
SDinput is a desired image SD the operator wishes to obtain as the final image,
mAs is a time-integrated tube current (sec) used as the reference,
t is a scan speed (sec),
PkV is a coefficient corresponding to a tube voltage,
Psl is a coefficient corresponding to an imaging slice thickness,
PHP is a coefficient corresponding to the helical pitch,
PFW is a coefficient corresponding to a ratio of an image slice thickness with respect to an imaging slice thickness,
PFC is a coefficient corresponding to a reconstruction function,
Pmode is a coefficient corresponding to a normal mode or a low dose mode as to X-ray exposure,
$\mu$ an X-ray absorption coefficient of water,
DPa is a water equivalent thickness (mm) used as the reference, and
DPb is a water equivalent thickness (mm) equivalent to the subject's body thickness.

13. An X-ray computed tomographic apparatus, comprising:
an X-ray tube;
a gantry configured to acquire projection data of an arbitrary range in a body axial direction of a subject by continuously moving a tabletop on which said subject is laid down and by continuously rotating said X-ray tube about said subject;
a reconstructing portion configured to reconstruct image data from said acquired projection data;
tube current value determining portion configured to determine plural tube current values respectively corresponding to plural positions within said range, on the basis of an image quality level specified or selected by an operator; and
a display portion configured to display a graph showing a spatial change of tube current values corresponding to said plural tube current values;
wherein a particular tube current value, $I_b$, is determined on the basis of SD (SDinput), mAs, PkV, Psl, PFW, PFC, SDa, t, PHP, Pmode, $\mu$, DPa, and DPb,
where SDa is an image SD of an image of a water phantom having a water equivalent thickness DPa used as the reference, taken and reconstructed with the use of a reference tube current, a reference tube voltage, a reference imaging slice thickness, and a reference image slice thickness, and a reference reconstruction function,
SDinput is a desired image SD the operator wishes to obtain as the final image,
mAs is a time-integrated tube current (sec) used as the reference,
t is a scan speed (sec),
PkV is a coefficient corresponding to a tube voltage,
Psl is a coefficient corresponding to an imaging slice thickness,
PHP is a coefficient corresponding to the helical pitch,
PFW is a coefficient corresponding to a ratio of an image slice thickness with respect to an imaging slice thickness,
PFC is a coefficient corresponding to a reconstruction function, Pmode is a coefficient corresponding to a normal mode or a low dose mode as to X-ray exposure, μ an X-ray absorption coefficient of water, DPa is a water equivalent thickness (mm) used as the reference, and DPb is a water equivalent thickness (mm) equivalent to the subject's body thickness.

14. An X-ray computed tomographic apparatus, comprising:

a gantry configured to acquire projection data related to a subject;

a reconstructing portion configured to reconstruct image data from said acquired projection data;

a sample image storage portion configured to store data of plural sample images corresponding to plural image quality levels; and a display portion configured to display a sample image corresponding to an image quality level selected by an operator.

15. An X-ray computed tomographic apparatus, comprising:

an X-ray tube;

a gantry configured to acquire projection data related to a subject;

a reconstructing portion configured to reconstruct image data from said acquired projection data according to reconstruction processing selected by an operator from plural types of reconstruction processing; and a tube current value determining portion configured to determine a tube current value on the basis of said selected type of reconstruction processing and an image quality level specified or selected by said operator;

wherein a particular tube current value, $I_b$, is determined on the basis of SD (SDinput), mAs, PkV, Psl, PFW, PFC, SDa, t, PHP, Pmode, μ, DPa, and DPb, where SDa is an image SD of an image of a water phantom having a water equivalent thickness DPa used as the reference, taken and reconstructed with the use of a reference tube current, a reference tube voltage, a reference imaging slice thickness, and a reference image slice thickness, and a reference reconstruction function, SDinput is a desired image SD the operator wishes to obtain as the final image, mAs is a time-integrated tube current (sec) used as the reference, t is a scan speed (sec), PkV is a coefficient corresponding to a tube voltage, Psl is a coefficient corresponding to an imaging slice thickness, PHP is a coefficient corresponding to the helical pitch, PFW is a coefficient corresponding to a ratio of an image slice thickness with respect to an imaging slice thickness, PFC is a coefficient corresponding to a reconstruction function, Pmode is a coefficient corresponding to a normal mode or a low dose mode as to X-ray exposure, μ an X-ray absorption coefficient of water, DPa is a water equivalent thickness (mm) used as the reference, and DPb is a water equivalent thickness (mm) equivalent to the subject's body thickness.

16. An X-ray computed tomographic apparatus, comprising:

an X-ray tube;

a gantry configured to acquire projection data of an arbitrary range in a body axial direction of a subject by continuously moving a tabletop on which said subject is laid down and by continuously rotating said X-ray tube about said subject;

a reconstructing portion configured to reconstruct image data from said acquired projection data;

a tube current value determining portion configured to determine plural tube current values respectively corresponding to plural positions within said range, on the basis an image quality level specified or selected by an operator; and a control portion that dynamically controls a tube current of said X-ray tube in association with movement of said tabletop, according to said determined plural tube current values;

wherein a particular tube current value, $I_b$, is determined on the basis of SD (SDinput), mAs, PkV, Psl, PFW, PFC, SDa, t, PHP, Pmode, μ, DPa, and DPb, where SDa is an image SD of an image of a water phantom having a water equivalent thickness DPa used as the reference, taken and reconstructed with the use of a reference tube current, a reference tube voltage, a reference imaging slice thickness, and a reference image slice thickness, and a reference reconstruction function, SDinput is a desired image SD the operator wishes to obtain as the final image, mAs is a time-integrated tube current (sec) used as the reference, t is a scan speed (sec), PkV is a coefficient corresponding to a tube voltage, Psl is a coefficient corresponding to an imaging slice thickness, PHP is a coefficient corresponding to the helical pitch, PFW is a coefficient corresponding to a ratio of an image slice thickness with respect to an imaging slice thickness, PFC is a coefficient corresponding to a reconstruction function, Pmode is a coefficient corresponding to a normal mode or a low dose mode as to X-ray exposure, μ an X-ray absorption coefficient of water, DPa is a water equivalent thickness (mm) used as the reference, and DPb is a water equivalent thickness (mm) equivalent to the subject's body thickness.

* * * * *